(12) United States Patent
Korkor et al.

(10) Patent No.: US 7,144,386 B2
(45) Date of Patent: Dec. 5, 2006

(54) CATHETER INTRODUCER HAVING AN EXPANDABLE TIP

(75) Inventors: Adel B. Korkor, Hartland, WI (US); Stephen Ash, West Lafayette, IN (US); Robert J. Kruger, McHenry, IL (US)

(73) Assignee: AB Korkor Medical, Inc., Hartland, WI (US)

( * ) Notice: Subject to any disclaimer, the term of this patent is extended or adjusted under 35 U.S.C. 154(b) by 280 days.

(21) Appl. No.: 10/634,715

(22) Filed: Aug. 5, 2003

(65) Prior Publication Data

US 2004/0030319 A1    Feb. 12, 2004

Related U.S. Application Data

(63) Continuation-in-part of application No. 09/896,035, filed on Jun. 29, 2001, now abandoned.

(51) Int. Cl.
*A61M 5/178* (2006.01)
(52) U.S. Cl. .................. 604/164.03; 604/506; 604/160; 604/164.04; 604/164.05
(58) Field of Classification Search ............. 604/93.01, 604/104, 264, 164.01–164.11, 543, 523, 173, 604/506; 606/185, 198, 108, 190–192, 136, 606/167
See application file for complete search history.

(56) References Cited

U.S. PATENT DOCUMENTS 3,877,429 A    4/1975    Rasumoff
4,451,256 A *   5/1984    Weikl et al. ............ 604/164.03
5,057,083 A *   10/1991   Gellman .................. 604/164.1
6,183,443 B1    2/2001    Kratoska et al.

FOREIGN PATENT DOCUMENTS

| EP | 0 093 101 | 4/1983 |
|---|---|---|
| WO | WO 98/29026 | 7/1998 |
| WO | WO 99/17665 | 4/1999 |
| WO | WO 00/69350 | 11/2000 |

* cited by examiner

*Primary Examiner*—Nicholas D. Lucchesi
*Assistant Examiner*—Aamer S. Ahmed
(74) *Attorney, Agent, or Firm*—Boyle Fredrickson Newholm Stein & Gratz S.C.

(57) ABSTRACT

A catheter includes a body having an outer surface defining a lumen and an expandable tip on a distal end thereof. The tip includes an opening axially extending therethrough. Upon insertion of a device having a larger outer diameter than the inner diameter of the expandable tip, the opening permits passage of the device therethrough. The tip expands commensurately with a difference between the outer diameter of the device and the inner diameter of the expandable tip. The expandable tip includes a tubular wall having an axially extending weakened portion formed from (1) at least two axially aligned slit segments and (2) at least two axially aligned segments that are strengthened when compared to the slit segments. One of the strengthened segments is positioned between two of the slit segments. Another of the strengthened segments is formed between a distal-most slit segment and a distal end of the expandable tip.

39 Claims, 5 Drawing Sheets

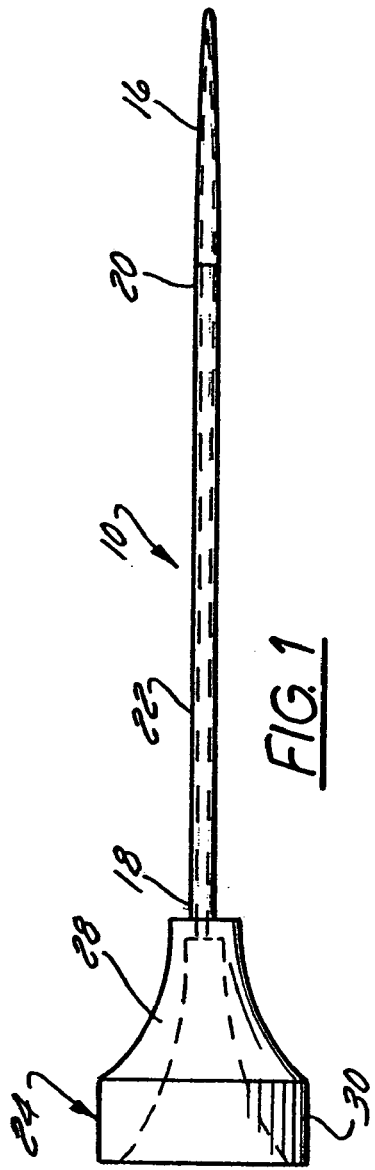
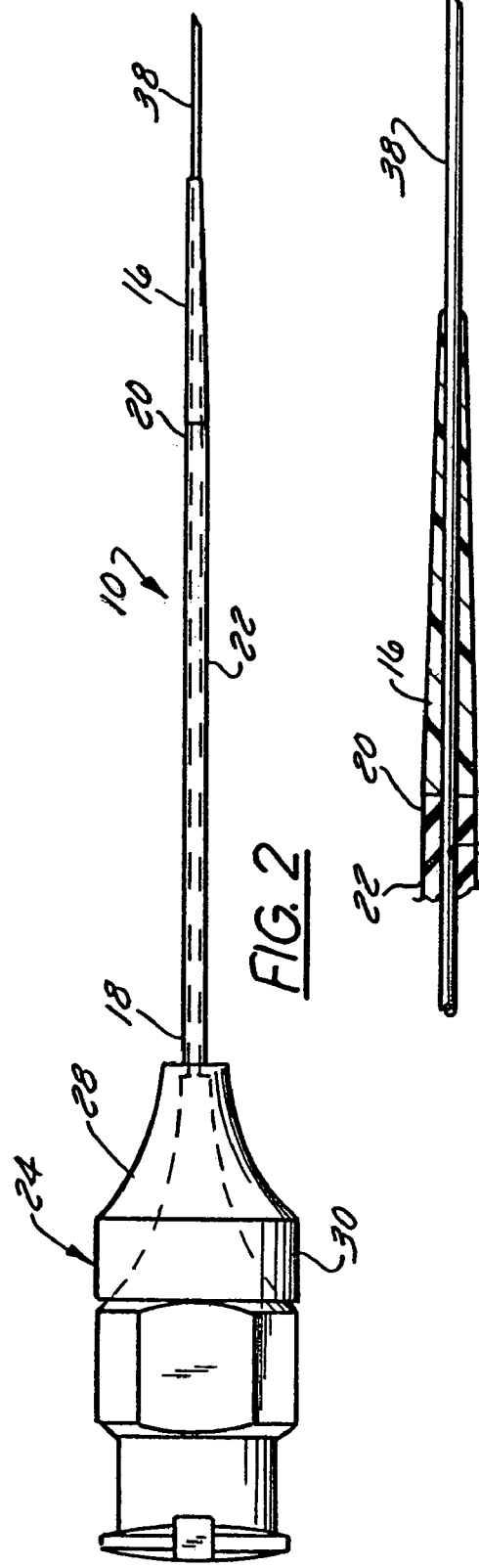
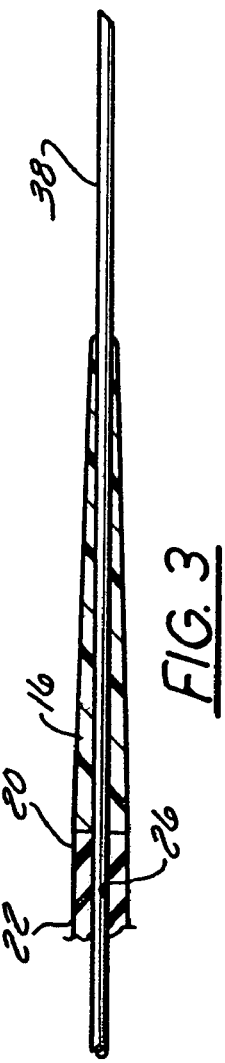

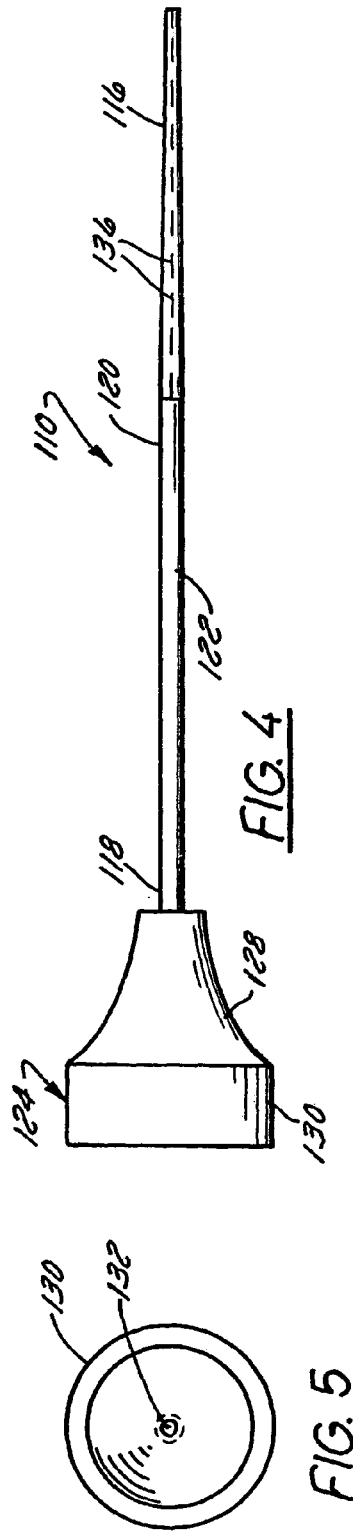
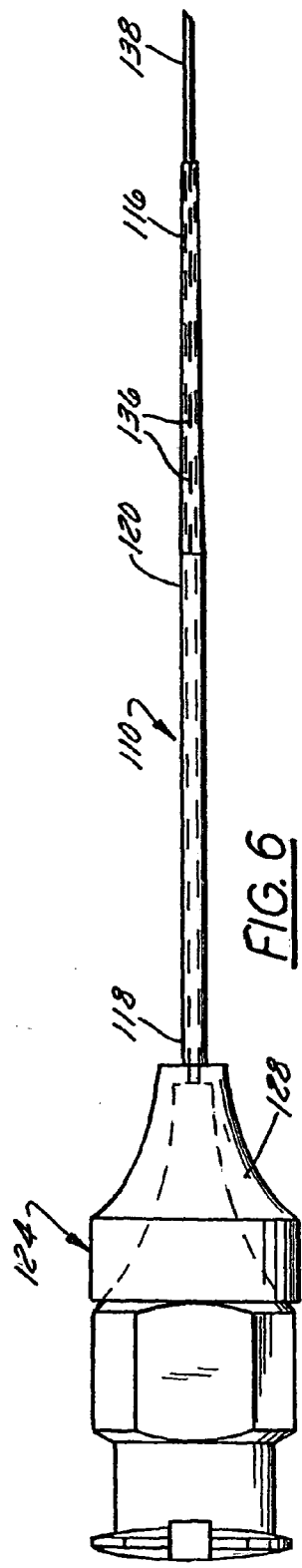
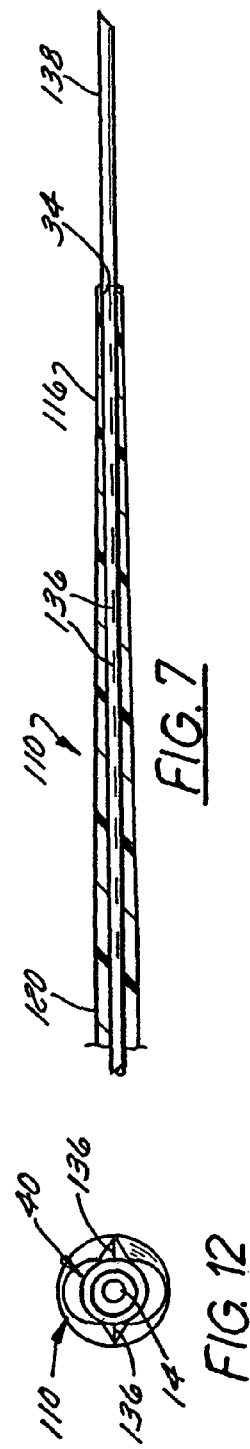

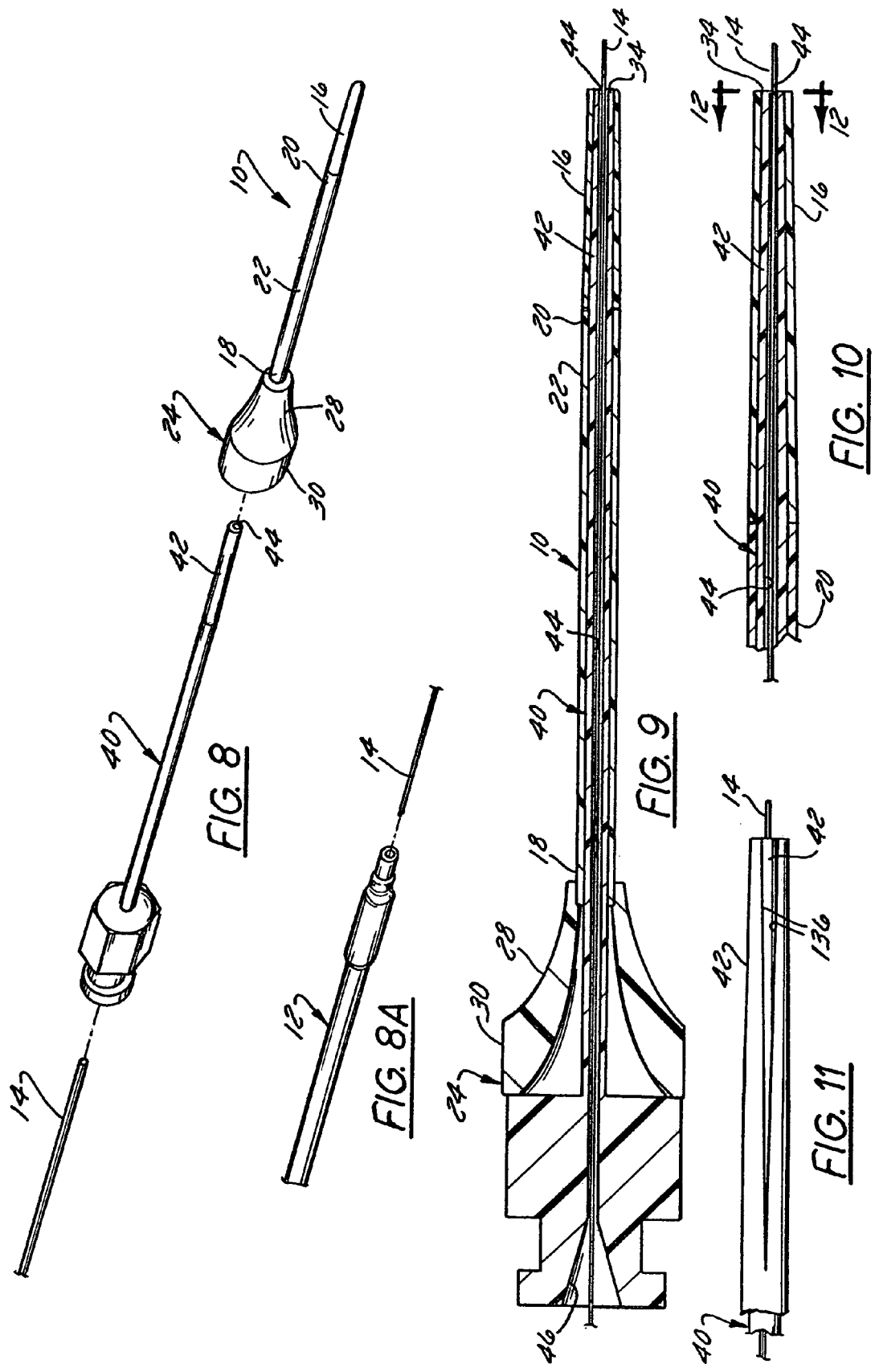

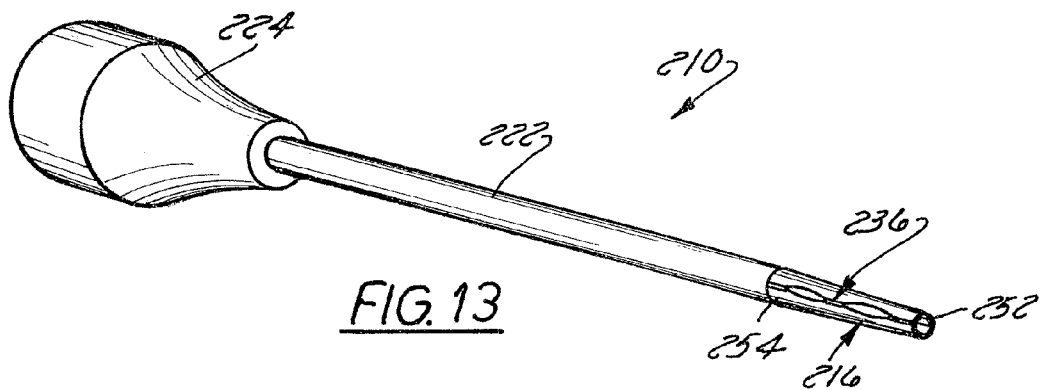
FIG. 13
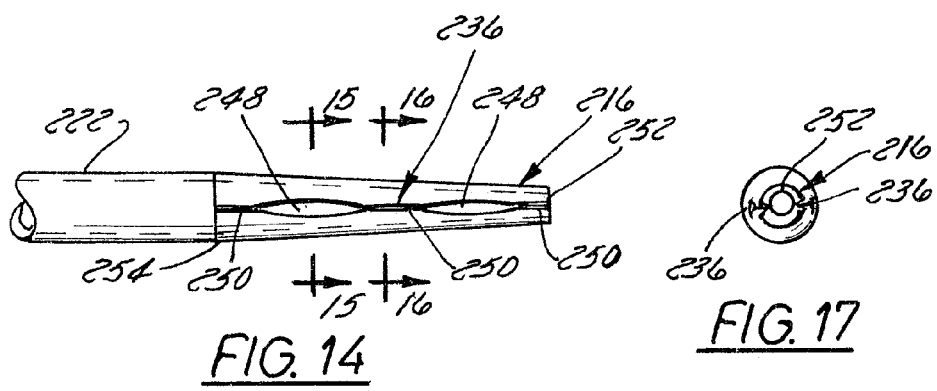
FIG. 14
FIG. 17
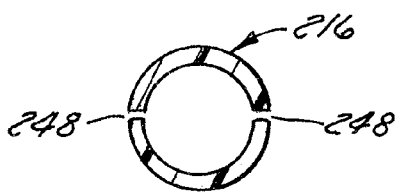
FIG. 15
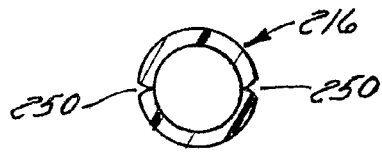
FIG. 16
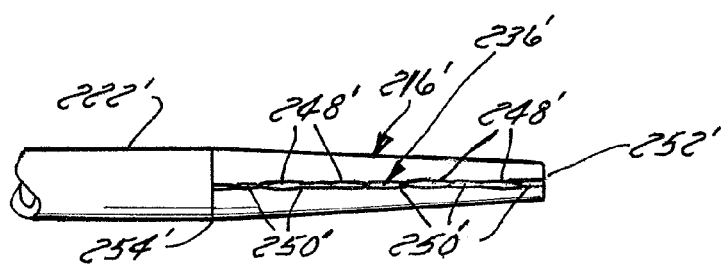
FIG. 18

CATHETER INTRODUCER HAVING AN EXPANDABLE TIP

CROSS REFERENCE TO RELATED APPLICATION

This application is a continuation-in-part of U.S. application Ser. No. 09/896,035; filed Jun. 29, 2001 now abandoned, that is entitled Catheter Introducer Having an Expandable Tip, the entire disclosure of which is incorporated herein by reference.

FIELD OF THE INVENTION

The invention relates to medical instruments, and in particular catheter introducers for introducing catheters and other medical devices into a patient's veins or arteries.

DESCRIPTION OF THE RELATED ART

Catheters are flexible tubes used for withdrawing fluids from or injecting fluids into a patient's body. For example, catheters can be used to introduce or withdraw fluids from a body cavity, duct, or vein, or artery (hereafter referred to as "blood vessels" for the sake of simplicity). They are used for a variety of purposes and for differing time periods.

Short-term catheters are used for only a brief period of time, e.g., for a matter of hours or a day or two. For example, a Swan-Ganz catheter is a large, hollow plastic tube (much like an IV catheter). It is placed in the side of the neck, the shoulder, or the groin area. The catheter is quite long and is advanced through the vein to the patient's heart. A lead of the Swan-Ganz is attached to a computerized monitor to allow doctors and nurses to gather information about how well the patient's heart is functioning. This information allows doctors to make decisions on the best way to treat the patient.

Long-term catheters are kept in the patient for longer periods of time, such as weeks or even months. Hickman catheters, for example, are catheters designed for long-term use in giving drugs and total parenteral nutrition and in withdrawing blood samples. Hickman catheters are used during, for example, bone marrow transplantations.

Catheter introducers are used to introduce short-term catheters, long-term catheters, and other peripheral and central venous or arterial devices into a blood vessel. They typically are threaded into the vessel and then act as a guide for introducing the peripheral or central venous or arterial devices into the vessel through the hollow interior of the catheter introducer.

Peripheral and central venous or arterial devices that can be introduced via a catheter introducer include, but are not limited to, single or double lumen catheters, declotting devices, Swan-Ganz catheters, balloon catheters, and hemodialysis catheters.

Conventional catheter introducers generally include a thin-walled tube, commonly known as a sheath. The distal end of the sheath is inserted through the skin into the blood vessel. A hub or valve housing is attached to the proximal end of the tube and contains a valve and seal structure through which a device, such as a catheter, is inserted into the tube and then into the blood vessel. The catheter introducer is advanced, in a sometimes serpentine path, through various blood vessels to place the catheter tip in the desired position. The thin walled tube, which extends for a short distance in the lumen of the blood vessel, protects the blood vessel adjacent the entrance site against perforation and abrasion from the catheter or other venous or arterial device during its insertion and placement, and together with the valve and seal structure, maintains a fluid-tight relationship with the blood vessel to prevent leakage.

To insert the conventional catheter introducer into the blood vessel, in one conventional method, a Seldinger type needle is used to pierce a path through the skin and underlying tissue into the blood vessel. A guidewire is inserted through the needle and into the blood vessel, after which the needle is withdrawn over the guidewire. Then, a tubular dilator is advanced over the guidewire and removed. The hemodialysis or other central or peripheral venous catheter is advanced over the guidewire. The guidewire is then removed.

Catheter introducers that are radially expandable have been proposed. For example, in U.S. Pat. No. 5,447,503, a guiding catheter tip with an expandable lumen is disclosed. The tip is made from a sidewall with a slot therein. One portion of the sidewall slides under another portion of the sidewall at the slot, forming a spiral or convoluted fold tip. The construction of this catheter, however, is complex, and requires the formation of the spiral fold tip.

Another catheter introducer, which is disclosed in U.S. Pat. No. 5,997,508, includes an introducer sheath that is expandable throughout its entire length. The introducer sheath has a wall that is folded to form a detent and an expandable leaflet. This introducer sheath requires insertion of an inner tube to expand the introducer sheath. The construction of this catheter introducer is also complex.

A combined dilator/catheter introducer is disclosed in U.S. Pat. No. 5,395,341. The dilator/catheter introducer has a tapered, distal portion that is made of a material that has a temperature dependent memory. The material changes shape when the temperature thereof is increased to body temperature so that the tapered, distal portion can change from its first, tapered shape to a second, expanded shape with a diameter close to the diameter of a proximal portion. Thus, this dilator/catheter introducer provides expansion of its tip, but only from a first diameter to a second, fixed diameter, with no gradation of the expansion.

In view of the foregoing, it would be desirable to provide a catheter introducer that has a tip that selectively expands upon insertion of a guidewire, dilator, or other device and only as much as is required to accommodate the passage of the device having a larger O.D. than the I.D. of the catheter introducer.

It would also be desirable to provide an improved method of introducing a catheter or other peripheral or central venous device into a blood vessel.

SUMMARY OF THE INVENTION

The invention, which is defined by the claims set out at the end of this disclosure, is intended to solve at least some of the problems noted above. A catheter introducer is provided that is designed to permit the insertion and withdrawal of a guidewire or other device that has an outer diameter (O.D.) greater than the inner diameter (I.D.) of the tip of the catheter introducer. The catheter tip of the catheter introducer is radially expandable upon insertion of the larger O.D. device to permit its passage through the catheter tip.

The catheter includes a body that includes an outer surface defining a lumen. The catheter has a proximal end and a distal end. A hub may be disposed at the proximal end of the catheter body. The hub allows insertion of devices into the catheter introducer. An expandable tip is disposed at the distal end of the catheter introducer and includes an axially extending opening therein. The opening of the expandable tip is configured to expand upon insertion of the larger O.D. device, but only enough to permit its passage through the catheter tip.

In a first preferred embodiment of the catheter introducer, the expandable tip is made from a material that becomes pliable based on temperature. At a lower temperature, such as room temperature, the tip material is rigid, and the tip can be threaded through a patient's venous or arterial system. Once inside the patient, the tip material becomes pliable as the patient's body temperature warms the material. The pliability allows for radial expansion of the tip such that the diameter of the opening of the tip can increase to accommodate insertion of devices having a range of O.D.s. Thus, at the higher temperature, a device with a larger O.D. than the I.D. of the tip of catheter introducer can be inserted through the opening of the pliable tip.

In a second preferred embodiment of the expandable catheter tip, the tip includes score lines, which weaken the structural integrity of the expandable tip. Insertion of a guidewire, dilator, or other device having a larger O.D. than the I.D. of the catheter tip expands or even ruptures along the score lines to permit the passage of the device.

In a third preferred embodiment of the expandable catheter introducer, the catheter introducer includes a body having an outer surface defining a lumen and having a proximal end and a distal end. The catheter introducer also includes an expandable tip on the distal end. The expandable tip includes a sidewall that is continuous and non-convoluted in an unexpanded state and includes an opening axially extending therethrough. Upon insertion of a device having a larger outer diameter than the inner diameter of the expandable tip, the opening is configured to permit passage of the device therethrough. The expandable tip is configured to expand commensurately with a difference between the outer diameter of the device and the inner diameter of the expandable tip. The expandable tip comprises a tubular wall having an axially extending weakened portion formed from (1) at least two axially aligned slit segments and (2) at least two axially aligned segments that are strengthened when compared to the slit segments. One of the strengthened segments is positioned between two of the slit segments. Another of the strengthened segments is formed between a distal-most slit segment and a distal end of the expandable tip.

A method of using the catheter is also provided. In a preferred embodiment of the method, a guidewire or other device having a larger O.D. than an initial, unexpanded I.D. of a catheter tip is inserted through an opening in the catheter tip. This is accomplished by first cannulating a blood vessel with a needle. The catheter introducer described above is advanced over the needle. The relatively rigid, thin distal tip of the catheter introducer facilities insertion and minimizes discomfort and risk of injury to the patient during this insertion. The needle is then withdrawn, and a guidewire, dilator, or other device is inserted into the proximal end of the catheter introducer through the opening of the hub. The device is then axially extended through the lumen of the body and passed through the opening of the expandable tip to expand the opening and the surrounding tissue sufficiently to permit subsequent passage of the venous device. The catheter introducer is then withdrawn, and a catheter or other peripheral or central arterial or venous device is inserted through the passage in the patient's body and into the blood vessel over a guidewire that either is part of or constitutes the device previously inserted into the catheter introducer.

In another preferred embodiment of the method, a vein or artery is cannulated with a needle and the catheter introducer, with the catheter introducer being disposed over the needle. The catheter introducer includes an expandable tip on the distal end. The expandable tip includes a body including an outer surface defining a lumen and having a distal end and a proximate end; and an expandable tip on the distal end. The expandable tip includes an opening axially extending therethrough and an axially extending weakened portion formed from (1) at least two axially aligned slit segments and (2) at least two axially aligned segments that are strengthened when compared to the slit segments. One of the strengthened segments is positioned between the slit segments. Another of the strengthened segments is formed between a distal-most slit segment and a distal end of the expandable tip. The needle is removed from the catheter introducer. A device having a larger outer diameter than a minimum inner diameter of the expandable tip is inserted into the body. The device is inserted through the lumen of the body. The device is inserted through the opening of the expandable tip, thereby expanding the expandable tip as a result of the insertion of the device through the tip. Then, the catheter introducer is removed from the patient's body while leaving the device in place.

The catheter introducer described herein allows a device having a larger O.D. than the initial unexpanded I.D. of the catheter tip to be inserted through the opening of the catheter tip with a single needle stick. The catheter tip is made from a material that allows threading of the catheter through the patient's venous or arterial system without bunching. The material does not damage tissue of the patient. It also has a much smaller initial tip diameter than conventional catheter introducers. The catheter introducer described herein is of relatively simple construction, providing a lower cost of manufacture when compare to more complex designs.

BRIEF DESCRIPTION OF THE DRAWINGS

Preferred exemplary embodiments of the invention are illustrated in the accompanying drawings, in which like reference numerals represent like parts throughout and in which:

FIG. 1 is a side elevation view of a catheter introducer including an expandable tip made in accordance with a first preferred embodiment of the invention;

FIG. 2 is a side elevation view of the catheter introducer of FIG. 1, with a syringe inserted therethrough;

FIG. 3 is an enlarged view of a distal end of the catheter introducer of FIG. 2;

FIG. 4 is a side elevation view of a catheter introducer including an expandable tip made in accordance with a second preferred embodiment of the invention;

FIG. 5 is a rear elevation view of the catheter introducer of FIG. 4;

FIG. 6 is a side elevation view of the catheter introducer of FIG. 4, with a syringe inserted therethrough;

FIG. 7 is an enlarged view of a distal end of the catheter introducer of FIG. 6;

FIG. 8 is an exploded perspective view of the catheter introducer of FIGS. 1–3, a dilator, which can be used to expand the catheter tip, a guidewire, which can be used to guide a venous device into a patient's vein or artery, and a venous device;

FIG. 8A is an exploded perspective view of the guidewire of FIG. 8 and a venous catheter that can be threaded over the guidewire;

FIG. 9 is an enlarged cross sectional view of the catheter introducer of FIGS. 1–3, a dilator, and a guidewire in the assembled state;

FIG. 10 is an enlarged side sectional view of the catheter introducer of FIGS. 1–3, a dilator, and a guidewire in the assembled state;

FIG. 11 is a side elevation view of the catheter introducer of FIGS. 4–7, a dilator, and a guidewire in the assembled state;

FIG. 12 is a cross sectional view through lines 12—12 of FIG. 10;

FIG. 13 is a perspective view of a catheter introducer including an expandable tip made in accordance with a third preferred embodiment of the invention;

FIG. 14 is an enlarged view of a distal end portion of the catheter introducer of FIG. 13;

FIG. 15 is a cross-sectional view along line 15—15 of FIG. 14;

FIG. 16 is a cross-sectional view along line 16—16 of FIG. 14;

FIG. 17 is an end view of the catheter introducer of FIG. 13;

FIG. 18 is an enlarged view of a distal end of a catheter introducer including an expandable tip made in accordance with a variant of the third preferred embodiment of the invention and differing from the catheter introducer shown in FIG. 13 in that it includes more slits along each score line;

Figure 19:
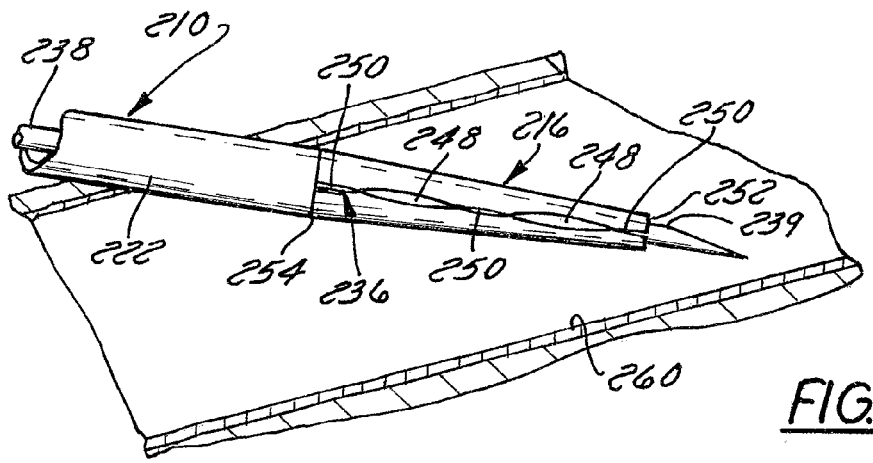
FIG. 19 is a cross-sectional view of a vein into which the catheter introducer of FIG. 13 and a needle are introduced.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

1. Resume

Pursuant to the invention, a catheter introducer is provided that can be used to introduce a relatively large central or peripheral venous or arterial device (hereafter collectively and individually referred to as a "venous device") into a patient's vein, artery, or the like (hereafter collectively and individually referred to as a "blood vessel") with a single stick from a small-gauge needle. For instance, the invention can be used to introduce an adult catheter having a diameter of 16 gauge or larger into a patient's vein or artery using a 20 to 22 gauge needle. The catheter introducer includes a catheter body having an outer surface defining a lumen. The catheter body has a proximal end and a distal end. An expandable tip is disposed at the distal end and includes an axially extending opening therethrough.

The expandable tip of one embodiment includes score lines and through-cut lines at the tip of the catheter introducer. The score lines both 1) provide column strength to the tip to prevent it from collapsing when the catheter introducer is inserted into a patient and/or when a guidewire or other device is inserted into the introducer, and 2) provide relatively easy splitting of the catheter introducer when a device, such as a guidewire, is inserted into the catheter introducer.

In use, a device, such as a guidewire, possibly supplemented by a dilator, and having a larger outer diameter than the inner diameter of the tip portion of the catheter introducer, can be threaded through into the catheter introducer from the proximal end. The opening of the expandable tip radially expands upon passage of the device through the opening. The catheter introducer can then be removed from the patient's body, and a relatively large diameter venous device can be safely guided into the blood vessel over the guidewire.

2. First Preferred Embodiment of Catheter Introducer

The catheter introducer described herein can be used for introducing into a patient's body a device having a larger outer diameter (O.D.) than the inner diameter (I.D.) of a tip of the catheter introducer in order to facilitate safe insertion of a venous device into the patient's body. Examples of venous devices that can be introduced with the aid of the catheter introducer include, but are not limited to, a single or double lumen catheter, a declotting device, a Swan-Ganz catheter, or a hemodialysis catheter.

A preferred embodiment of the catheter introducer 10 is illustrated in FIGS. 1–3. The catheter introducer 10 includes (1) a proximal end 18, which is the end that is near, e.g., the physician or other caregiver, and (2) a distal end 20, which is the end that is spaced from the caregiver. The distal end 20 is inserted into a patient. The catheter introducer 10 also includes a catheter body 22, a hub 24, and an expandable tip 16.

The catheter body 22 preferably is formed from a medical grade natural or synthetic rubber or a plastic such as fluorinated ethylene-propethylene (FEP), polyethylene (PE), or the like. It is elongate, tubular, and includes an outer surface defining a lumen 26 that extends longitudinally through the catheter body 22. In a preferred embodiment, the lumen 26 narrows from the proximal end 18 to the distal end 20 of the catheter body 22, e.g., narrowing from 14–18 gauge at the proximal end to 20–22 gauge at the distal end 20. However, the catheter introducer 10 can have different diameters, depending on the ultimate use of the catheter introducer 10. For example, a smaller diameter catheter introducer 10, narrowing, for example, from 18–20 gauge at the proximal end to 22–26 gauge at the distal end, can be used for a pediatric catheter. The length of the catheter introducer 10 depends on the use of the catheter introducer 10 and, more particularly, on the depth that the catheter introducer 10 is to be inserted into the patient. For instance, the catheter body 22 may be about 2.5 inches long for a central catheter or about 1.5" long for a peripheral catheter. The hub 24, which is located at the proximal end 18 of the catheter body 22, preferably is formed from a medical grade plastic. The hub 24 may additionally include valve and seal structure(s) (not shown) to prevent fluids from leaking out of the catheter introducer 10. The hub 24 may also include a hollow, cone-shaped portion 28 with a collar 30 that extends axially from the wider side of the cone-shaped portion 28. The hub 24 is connected to the catheter body 22 at the narrow, distal end of the cone-shaped portion 28 in a conventional manner. An opening 32 (FIG. 5) projects axially through the hub 24. The opening 32 allows the hub 24 to be placed in communication with the catheter body 22, such that other devices can be inserted into the catheter introducer 10 via the opening 32 in the collar 30 and the cone-shaped portion 28 to reach the lumen 26 of the catheter body 22.

The expandable tip 16 is located at the distal end 20 of the catheter body 22. The expandable catheter tip 16 is made from a material that has the combined properties of being both sufficiently flexible to permit bending when the catheter tip 16 encounters a curve in the vessel or the like, yet sufficiently rigid to allow the catheter tip 16 to be threaded through the vessel. The catheter tip 16 includes a continuous and non-convoluted sidewall. The sidewall is smooth and curved without any folds or slits, therein, making the tip 16 relatively easy to manufacture when compared to previous tips. The sidewall preferably is circular in transverse cross section, but could be oblong as well. The open interior of the tip 16 forms an axially extending opening 34 therein for receiving a device in the form of a guidewire and possibly a dilator as detailed below.

Still referring to FIGS. 1–3, in the first preferred embodiment, the tip 16 of the catheter introducer 10 is formed from a thermal softening material that is relatively rigid at room temperature. The tip 16 is fused to the distal end of the catheter body 22. In a preferred embodiment, the expandable tip 16 is ¾" long and is formed from PE or polyurethane. However, the length of the tip 16 and of the body 22 can vary to meet the needs of a particular application. When the catheter introducer 10 is initially inserted into the patent's vessel, the catheter tip 16 is relatively rigid such that the catheter tip 16 can be threaded into and through the patient's blood vessel without bunching. It is also relatively narrow, typically having an initial diameter of about 20–22 gauge needle for an adult catheter and 20–26 gauge for a pediatric catheter. The relatively narrow tip 16, especially one that is tapered as illustrated, is far less invasive to the patient than a conventional catheter introducer, which has a diameter of 14–18 gauge. It is also easier to thread through the patient's venous system.

The softenable material of the tip 16 becomes pliable when it warms to or near body temperature, at or about 30° C. to 37° C. Upon pressure from a guidewire or other device, the pliability allows for radial expansion of the tip 16 such that the I.D. of the tip 16 increases to accommodate passage of devices having a larger O.D. than the I.D. of the catheter tip 16 as seen in FIG. 9. The extent of the radial expansion is determined by the O.D. of the device being forced through the tip 16. Thus, a device having a larger O.D. will cause the opening 34 of the tip 16 to expand more than a device having a smaller O.D. A 20 gauge diameter tip could expand sufficiently to accept a 14–18 gauge guidewire, dilator, or other device.

3. Second Preferred Embodiment of the Expandable Catheter Tip

Referring now to FIGS. 4–7, a catheter introducer 110 is illustrated that differs from the catheter introducer 10 of the first embodiment primarily in that it has a different type of expandable tip 116. Elements of the catheter introducer 110 of FIGS. 4–7 corresponding to elements of the introducer 10 of FIGS. 1–3 are, accordingly, designated by the same reference numerals, incremented by 100. The introducer 110 therefore includes a body 122, a hub 124, and a tip 116.

In this preferred embodiment, the expandable catheter tip 116 is made of the same material as the catheter body 122, and the continuous and non-convoluted catheter tip 116 includes score lines 136 that extend partially or completely through the depth of the catheter tip 116. The material of the body and tip may, for example, comprise polytetrafluoroethylene (PTFE), FEP, or PE. The score lines 136 weaken the structural integrity of the catheter tip 116 so as to permit the catheter tip 116 to expand or even split along the score lines 136 upon passage of a device 14 or 40 having a larger O.D. than the initial I.D. of the catheter tip 116. The score lines 136 preferably extend axially along the outer surface of the catheter tip 116. In the illustrated embodiment, two sets of score lines 136 are included and are located on opposite sides of the catheter tip 116. Preferably, 30% to 100% of the length of the catheter introducer 110 includes the score lines 136. More preferably, 30% to 50% of the length of the catheter introducer 110 includes the score lines 136. The depth of the score lines 136 may vary, depending on the application, from 20% to 100%, and preferably 30% to 60%, of the depth.

Upon insertion of a device having a larger O.D. than the initial I.D. of the tip 116, the score lines 136 expand or even rupture as seen in FIGS. 11 and 12, permitting expansion of the tip sufficiently to cause its O.D. sufficiently to permit passage of the device through the opening 134.

4. Third Preferred Embodiment of the Expandable Catheter Tip

Referring now to FIGS. 13–20, a catheter introducer 210 is illustrated that differs from the catheter introducer 110 of the second embodiment primarily in that it has a different type of expandable tip 216. Elements of the catheter introducer 210 of FIGS. 13–20 corresponding to elements of the introducer 110 of FIGS. 4–7 are, accordingly, designated by the same reference numerals, incremented by 100. The introducer 210 therefore includes a body 222, a hub 224, and a tip 216. The tip 216 is about ½" long and tapered as described above, preferably having a maximum inner diameter (ID) of about 0.04" at its proximal end 254 and a minimum ID of about 0.031 at its distal end 252. The tip 216 also has one or more axially extending weakened portions 236 that split when a larger diameter object is threaded through the catheter introducer 210. The catheter introducer 210 preferably includes two weakened portions 236 offset by 180°, although other offsets are possible. In addition, less or more than two weakened portions 236 can be provided. Preferably, the weakened portions 236 are formed in an outer peripheral surface of the tip 216 as opposed to the inner peripheral surface.

The expandable catheter tip 216 of this embodiment differs from the expandable tip 116 of the second embodiment primarily in that the tip 116 had weakened portions in the form of continuous score lines 136, whereas each weakened portion 236 of the tip 216 includes a serious of slit segments 248 separated from one another by strengthened segments 250. Each weakened portion 236 preferably additionally includes 1) a strengthened segment 250 between the distal end 232 of the tip 216 and the distal end of the most distal slit segment 248, and 2) a strengthened segment 250 between a proximal end of the most proximal slit segment 248 and the proximal end 254 of the tip 216. The slit segments 248 and strengthened segments 250 of each weakened portion 236 extend axially of the tip 216 and are disposed collinearly with each other. This combination of slit segments and strengthened segments provides an ideal balance between splittability and strength.

Specifically, the split segments 248 of each weakened portion 236 reduce the strength of the weakened portion 236 sufficiently to permit the tip 216 to split with relatively little resistance when a larger diameter instrument such as a guidewire passes through the tip 216. The resistance to expansion decreases proportionally with the percentage of the tip length that is split. Hence, the longer the combined length of the slit segments 248, the greater the ability of the introducer 210 to accept guidewires or other devices having a diameter significantly larger than the diameter of the distal end 252 of the tip 216.

On the other hand, the strengthened segments 250 of each weakened portion 236 overcome at least two problems that would be presented if the slit segments 248 were to extend uninterrupted along the full length of the tip 216. First, by forming the extreme distal end of each weakened portion 236 from a strengthened segment 250 rather than a slit segment 248, the distal end 252 of the tip 216 is sufficiently strong to prevent the catheter introducer 210 from splitting and peeling back like a banana peel upon insertion of the catheter introducer into a patient's body. Second, by separating the slit segments 248 from one another and providing at least one strengthened segment 250 between them, the column strength of the tip 216 is increased, hence inhibiting or preventing radial expansion and axial collapse (i.e., "bunching") of the tip 216 that could otherwise occur upon the insertion of a larger diameter object into the tip 216 and/or upon insertion of the introducer 210 into the patient's body.

One or more of the strengthened segments 250 of each weakened portion 236 could be formed from an unaltered (i.e., full thickness) portion of the tip wall. However, at least the distal-most strengthened segment 250, and preferably all strengthened segments 250, preferably take the form of scored segments of reduced thickness when compared to the un-weakened portions of the tip wall. The scored segments 250 each provide a weakened segment that will still break upon the insertion of a larger diameter object to permit the tip 216 to expand but still provide the column strength required to prolong premature splitting of the distal end 252 of the tip or radial collapse and axial expansion of the intermediate portion of the tip 216.

The number of slit segments 248, length of each slit segment 248, and spacing between them, and the resulting number, length, and spacing of the strengthened segments 250 will vary depending on several factors. These factors include, inter alia, the material of the introducer 210 and the desired balance to be struck between ease of tip splitting and resistance to tip splitting. In the embodiment of FIGS. 13–17 in which the tip 216 is 0.5" long, each weakened portion 236 preferably includes two spaced slit segments 248, each of which is approximately 0.1" to 0.2", and three scored segments 250, each of which is about 0.03" to 0.1" long. In a variant illustrated in FIG. 18, each weakened section 236' is formed from four slit segments 248', leaving a total of five scored segments 250' at the ends of the tip 216' and between the slit segments 248'. In this case, each slit segment 248' is about 0.07" to 0.1" long, and each scored segment 250' is about to 0.02" to 0.08" long. Perhaps counterintuitively, finite element analysis (FEA) has indicated that that the four-slit variant of FIG. 18 is actually weaker in tension than the two-slit embodiment of FIGS. 13–17 and thus more easily split. This may be advantageous from the physician's vantage point to the extent that the introducer will offer less resistance to the insertion of a guidewire or other inserted object hence facilitating insertion.

Referring again to FIGS. 13–17, the slit segments 248 extend at least essentially completely through the depth of the outer wall of catheter tip 216. The slit segments 248 can also extend completely through the depth of the catheter tip outer wall, although making such slits can dull the blade (not shown) that forms such slit segments 248, especially if the blade contacts a solid mandrel (not shown). Preferably, the slit segments 248 extend at least 90 percent, and more preferably about 99 percent, through the thickness of the tip outer wall. Hence, for a catheter introducer having a tip wall thickness of 0.010", the slit segments 248 preferably are about at least about 0.0090" deep, and more preferably about 0.0099" deep.

The scored segments 250, if present, preferably extend about ¼ to ½ through the depth of the tip wall. Hence, for a catheter introducer tip wall having a thickness of about 0.010", the scored segments 250 preferably have a depth of between 0.02" and 0.05".

In a preferred method of making the weakened portions 236 of the tip 216, the catheter introducer 210 is fitted over a mandrel (not shown). The mandrel can be solid or it can be keyed to include grooves that are aligned with cutting edges (not shown) of blades (also not shown). Preferably, continuous score lines are simultaneously cut into opposite sides of the tip 216. This simultaneous cutting from opposite sides advantageously tends to center the mandrel, as opposed to causing the mandrel to flex. The slit segments 248 may then be formed via a plunge cutting operation using blades that each includes a discontinuous or saw-tooth cutting edge. This cutting also is preferably performed by moving two blades toward opposite sides of the catheter introducer 210.

The slit segments 248 and scored segments 250 of each weakened portion 236 could alternatively be formed in a single step using a blade that forms both the slit segments 248 and the scored segments 250. For this operation, each blade would include a cutting edge that includes segments of two different lengths: longer ones to form the slit segments 248 and shorter ones to form the scored segments 250.

5. Operation of the Catheter Inserter

Typical use of the catheter inserter 10 of the first embodiment will now be described. Referring initially to FIGS. 2 and 3, the patient's vessel is first cannulated with a relatively small needle 38, such as a 21 or 22 gauge needle. In a preferred implementation of the method, a caregiver finds a vessel by inserting the needle 38 into an area containing the vessel of interest, such as a vein or artery in the neck, chest, or leg near the groin. Aspiration of blood should be obtained to ensure appropriate position within the vessel.

The catheter introducer 10 is then advanced over the needle 38, starting with the distal end 20 of the catheter introducer 10, until the catheter introducer 10 is inside the vessel. The catheter tip 16 is relatively rigid at this time such that the catheter tip 16 can be threaded into and through the patient's blood vessel without bunching. The relatively narrow tip 16 is also far less invasive to the patient than a conventional catheter introducer and easier to thread through the patient's venous system. The needle 38 is then removed from the catheter introducer 10, leaving the catheter introducer 10 in the patient's blood vessel.

Next, after the tip 16 warms and becomes pliable, the tip 16 can expand sufficiently to receive a guidewire and to create a passage in the patient's body that is sufficiently large to receive a venous device 12 (FIG. 8a) having a diameter larger than the initial diameter of the tip 16. Referring now to FIGS. 8 and 9–11, a dilator 40 can, if necessary, be used to radially expand the opening 34 of the tip 16 before or after the guidewire 14 is inserted into the catheter introducer 10. The dilator 40 has a distal end 42 made from a flexible, relatively elastic material, such that it can flex without becoming kinked or bent as it is inserted into the catheter introducer 10. The dilator 40 includes a bore 44 extending therethrough and an insertion port 46 at its proximal end to guide the guidewire 14 into dilator 40. It is conceivable, however, that the guidewire could be threaded through the catheter introducer 10 prior to introduction of the dilator 40, particularly if the guidewire 14 is relatively narrow and the dilator 40 is used primarily to expand the tip 16 sufficiently to accommodate passage of the subsequently-inserted venous device 12. Alternatively, a solid or hollow dilator may be inserted into the catheter introducer 10 to enlarge the tip 16 and then withdrawn prior to introduction of the guidewire.

Whether it is inserted before or after the guidewire 14, the dilator 40 is advanced through the catheter introducer 10, preferably with a twisting motion to assist its passage. As the dilator 40 passes through the tip 16, the opening 34 of the catheter tip 16 expands radially under pressure of the dilator 40, expanding the tip 16 from the configuration of FIGS. 1–3 to the configuration of FIG. 8 and expanding the O.D. of the tip 16 sufficiently to create a passage in the patient's body of sufficient diameter to receive the venous device 12. Significantly, the degree of expansion is determined primarily by the diameter of the dilator 40, not by any memory property of the tip 16, permitting the caregiver to carefully select the final diameter of the tip 16 simply by choosing a particular introducer/dilator combination.

After the guidewire 14 is in place in the blood vessel, the catheter introducer 10 is removed while the guidewire 14 is held securely to prevent dislodging it from the blood vessel. Next, the venous device 12 is threaded over the guidewire 14 and into the blood vessel. The guidewire 14 is removed, leaving the venous device 12 in place inside of the blood vessel. The venous device 12 can then be sutured or otherwise secured in place, if necessary.

As should be apparent from the above discussion, the dilator 40 is not required if the guidewire 14 is sufficiently rigid and wide to expand the tip 16 sufficiently to receive the venous device 12 after the catheter introducer 10 is removed from the patient's body.

Referring now to FIGS. 11 and 12, for a catheter introducer 110 having an expandable tip 116 of the second preferred embodiment, the guidewire 14 can be used to assist in the expansion or even rupturing of the tip 116 along the score lines 136, leading to expansion of the tip 116 of the second embodiment in much the same manner as the tip 16 of the first embodiment expands (compare FIG. 6 to FIGS. 11 and 12). For a catheter introducer 110 having an expandable tip 116 of the second preferred embodiment, no dilator should be needed. The use of the catheter introducer 110 of the second embodiment is otherwise identical to that of the catheter introducer 10 of the first embodiment and, accordingly, will not be detailed.

The catheter introducers 10, 110 described herein allows a cannulation of a blood vessel with a small needle 38, e.g., a 20–22 gauge needle for an adult catheter and 22–26 gauge for a pediatric catheter, and introduction of the catheter introducer 10 into the vessel. After a guidewire 14 and, if necessary, a dilator 40, is/are threaded through the catheter introducer 10 and the catheter introducer removed, a much larger venous device 12, e.g., a 14 gauge device, can be advanced into the blood vessel. This process is accomplished with a single stick from a relatively narrow needle.

Typical use of the catheter inserter 210 of the third preferred embodiment will now be described in conjunction with a guidewire, it being understood that a guidewire would not be required or even desired for all applications and that one or more of the insertion techniques described above in conjunction with the other embodiments, or even different insertion techniques entirely, could be employed. The insertion technique that will now be described could also be used with respect to the other embodiments described above.

Prior to insertion, the catheter introducer 210 is threaded over a needle 238 so that the needle protrudes beyond the distal end of the tip 216, with the distal end 252 of the tip 216 preferably being located 0.01" from the heel 239 of the needle 238, i.e., from the first point along the length of the needle 238 at which the needle's radial cross section is entirely solid. The needle 238 is small enough to fit through the tip 216 without splitting the tip. A 21 or 22 gauge needle will suffice for this purpose in the illustrated embodiment in which the tip 216 has a minimum ID of 0.031".

Next, the desired vessel 250 is cannulated with the introducer/needle assembly by puncturing the patient's skin 262 and inserting the assembly into the vessel 260 (using the needle tip to puncture the patient's skin (not shown) and vessel wall) until at least the distal end 252 of the tip 216, and preferably most or all of the tip 216, is positioned in the vessel 260 as illustrated in FIG. 19. If a portion of the tip 216 remains outside of the vessel 260, a small amount of blood may leak out of the introducer 210 through the slit segments 248. However, the volume of leaked blood would be so small as to amount to no more than minor bruising if the blood leaks under the patient's skin or a few drops if blood leaks outside of the patient's skin. This leakage would be of no danger to the patient.

Figure 20:
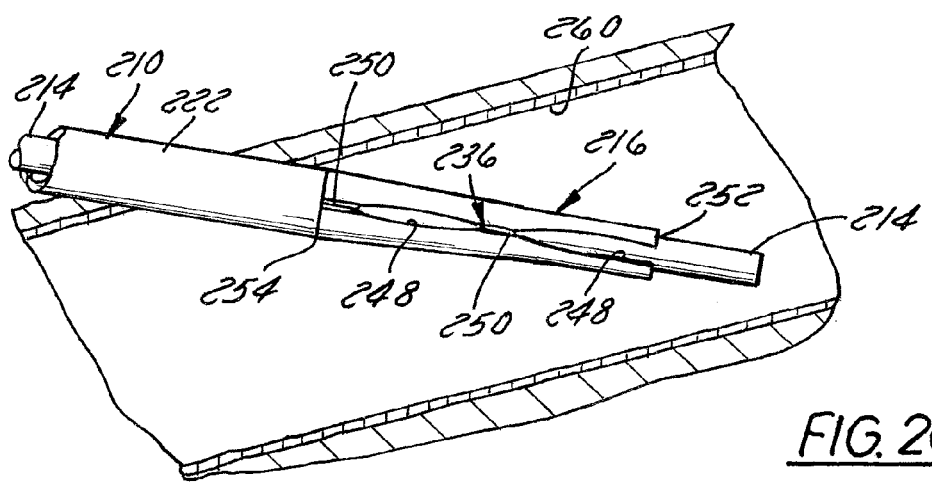
FIG. 20 is a cross-sectional view of the vein of FIG. 19 and the catheter introducer of FIG. 13, with a guidewire introduced into the catheter introducer, showing the guidewire beginning to split the catheter introducer.

Once the needle 238 and catheter introducer 210 are inserted into the vessel 260, the needle 238 is removed, leaving the catheter introducer tip 216 in the vessel 260. Referring now to FIG. 20, a device having a larger outer diameter than the inner diameter of the catheter introducer 210 is inserted into the catheter introducer 210. In FIG. 20, the device shown is a guidewire 214. The guidewire 214 ruptures the tip 216 along at least the distal-most scored segment 250 of one or more of the weakened portions 236 and expands at least the distal-most slit segment 248 of at least one of the weakened portions 236 to expand the diameter of the distal end 252 of the tip 216 sufficiently to receive the guidewire 214. In the illustrated embodiment in which a relatively small diameter (0.038") guidewire is employed, only the distal-most scored segment 250 ruptures. However, larger-diameter guidewires could be easily accommodated, with consequent more pronounced tip expansion, potentially resulting in rupturing of the scored segment 250 between the slit segment 248 and expansion of the tip 216 along the proximal slit segment 250. In this manner guidewires or other devices of vastly different diameters can be introduced using a single, small diameter needle.

Figure 21:
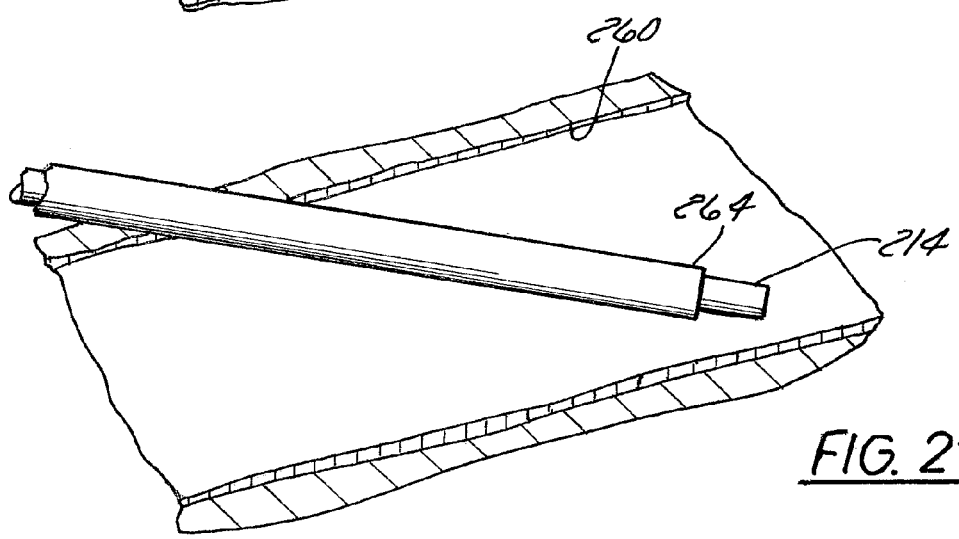
FIG. 21 is a cross-sectional view of the vein of FIG. 19, the guidewire of FIG. 19, and a medical device inserted over the guidewire.

Once the guidewire 214 is in place, the introducer 216 is removed, and a medical device 264 is threaded over the guidewire 214 and into the vessel as illustrated in FIG. 21. The device 264 may, for example, be a dilator or a PICC line, which is a special IV line used to provide fluids to a vein. The guidewire 214 is then removed by pulling it through the proximal end of the medical device 264, and the device 264 is used in its intended manner.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention.

The invention is not intended to be limited to the preferred embodiments described above, but rather is intended to be limited only by the claims set out below. Thus, the invention encompasses all alternate embodiments that fall literally or equivalently within the scope of these claims.

What is claimed is:

1. A catheter introducer, comprising:
   (a) a body including an outer surface defining a lumen and having a proximal end and a distal end; and (b) an expandable tip on the distal end, the expandable tip including a sidewall that is continuous and non-convoluted in an unexpanded state and including an opening axially extending therethrough and configured, upon insertion of a device having a larger outer diameter than the inner diameter of the expandable tip, to permit passage of the device therethrough, the expandable tip being configured to expand commensurately with a difference between the outer diameter of the device and the inner diameter of the expandable tip, wherein the expandable tip comprises a tubular wall having an axially extending weakened portion formed from (1) at least two axially aligned slit segments and (2) at least two segments that are axially aligned with one another and with the slit segments and that are strengthened when compared to the slit segments, one of the strengthened segments being positioned between two of the slit segments and another, distal-most strengthened segments being formed between a distal-most slit segment and a distal end of the expandable tip and being weakened when compared to portions of the tubular wall that are circumferentially adjacent to the distal-most strengthened segment.

2. The catheter introducer of claim 1, wherein at least one of the strengthened segments comprises a scored segment having a wall thickness greater than a thickness of the expandable tip wall at the slit segments but less than a thickness of the remainder of the expandable tip wall.

3. The catheter introducer of claim 2, wherein the slit segments and the scored segments are formed in an outer peripheral surface of the expandable tip wall.

4. The catheter introducer of claim 1, wherein the body is formed from a material comprising a polymeric material.

5. The catheter introducer of claim 1, wherein the weakened portion of the expandable tip comprises at least four axially aligned slit segments.

6. The catheter introducer of claim 1, wherein the tubular wall of the expandable tip has at least two axially extending weakened portions.

7. The catheter introducer of claim 6, wherein the two weakened portions are offset from one another by about 180°.

8. The catheter introducer of claim 1, wherein the slit segments extend at least essentially through the depth of the expandable tip wall.

9. The catheter introducer of claim 1, wherein the slit segments extend through at least about 90% through the depth of expandable tip wall.

10. The catheter introducer of claim 9, wherein the slit segments extend through at least about 99% of the depth the expandable tip wall.

11. The catheter introducer of claim 1, wherein at least one of the strengthened segments comprises a scored segment extending through about 10% of the depth of the expandable tip wall.

12. The catheter introducer of claim 11, wherein the scored segment extends through about 20% of the depth of the expandable tip wall.

13. The catheter introducer of claim 1, wherein all of the strengthened segments are weakened when compared to portions of the tubular wall that are circumferentially adjacent to the strengthened segments.

14. A catheter introducer, comprising:
(a) an elongate, hollow body having a distal end and a proximal end;

(b) a hub disposed at the proximate end, the hub being configured to permit communication between the hub and the body; and (c) a tip disposed at the distal end and including a sidewall that is continuous and non-convoluted in an unexpanded state and including an opening extending axially therethrough, the opening being selectively radially expandable to permit passage through the tip of a device having a larger outer diameter than the inner diameter of the tip, the tip being configured to expand commensurately with a difference between the outer diameter of the device and the inner diameter of the expandable tip, wherein the expandable tip comprises a tubular wall having an axially extending weakened portion formed from (1) at least two axially aligned slit segments and (2) at least two axially aligned segments that are strengthened when compared to the slit segments, one of the strengthened segments being positioned between the slit segments and another of the strengthened segments being formed between a distal-most slit segment and a distal end of the expandable tip, a distal-most one of the strengthened segments comprising a scored segment having a wall thickness greater than a thickness of the expandable tip wall at the slit segments but less than a thickness of the remainder of the expandable tip wall.

15. The catheter introducer of claim 14, wherein the body is tapered such that the distal end is narrower than the proximal end.

16. The catheter introducer of claim 14, wherein the slit segments are formed in an outer peripheral surface of the expandable tip wall.

17. The catheter introducer of claim 16, wherein the body is formed from a material comprising a polymeric material.

18. A method of inserting a medical device having a larger outer diameter than an inner diameter of a catheter tip of a catheter introducer through an opening in the catheter tip, the method comprising:

(a) cannulating a vein or artery with a needle and the catheter introducer, the catheter introducer being disposed over the needle and the catheter introducer including an expandable tip on a distal end thereof, the expandable tip including
(i) a body including an outer surface defining a lumen and having a distal end and a proximate end; and;
(ii) an expandable tip on the distal end, the expandable tip having a tubular wall, including an opening axially extending therethrough and an axially extending weakened portion formed from (1) at least two axially aligned slit segments and (2) at least two segments that are axially aligned with the slit segments and with one another and that are strengthened when compared to the slit segments, one of the strengthened segments being positioned between two of the slit segments and another, distal-most strengthened segment being formed between a distal-most slit segment and the distal end of the expandable tip and being weakened when compared to portions of the tubular wall that are circumferentially at to the distal-most strengthened segment, (b) removing the needle from the catheter introducer;
(c) inserting a medical device into the body, the device having a larger outer diameter than a minimum inner diameter of the expandable tip;
(d) inserting the medical device through the lumen of the body; and (e) inserting the medical device through the opening of the expandable tip, thereby expanding the expandable tip as a result of the insertion of the medical device through the tip; and then
(f) removing the catheter introducer from the patient's body while leaving the device in place.

19. The method of claim 18, wherein the device comprises a guidewire.

20. The method of claim 19, further comprising, after the removing step, inserting a peripheral or central venous or arterial device over the guidewire and into the vein or artery, and then removing the guidewire from the peripheral or central venous or arterial device.

21. The method of claim 19, wherein the peripheral or central venous or arterial device comprises a PICC line.

22. The method of claim 18, wherein the expanding step comprises splitting the distal end of the expandable tip at least one of the weakened portions and expanding a width of at least one of the slit segments.

23. The method of claim 18, wherein all of the strengthened segments are weakened when compared to portions of the tubular wall that are circumferentially adjacent to the strengthened segments.

24. A catheter introducer, comprising:
(a) a body including an outer surface defining a lumen and having a proximal end and a distal end; and
(b) an expandable tip on the distal end, the expandable tip including a sidewall that is continuous and non-convoluted in an unexpanded state and including an opening axially extending therethrough and configured, upon insertion of a device having a larger outer diameter than the inner diameter of the expandable tip, to permit passage of the device therethrough, the expandable tip being configured to expand commensurately with a difference between the outer diameter of the device and the inner diameter of the expandable tip,
wherein the expandable tip comprises a tubular wall having an axially extending weakened portion formed from (1) at least one slit segment and (2) at least first and second scored segments that are axially aligned with each other and with the slit segment, the first scored segment being positioned between a proximal-most slit segment and a proximal end of the expandable tip, and the second scored segment extending from a distal-most slit segment to a distal end of the expandable tip.

25. The catheter introducer of claim 24, wherein the slit segment and the scored segments are formed in an outer peripheral surface of the expandable tip wall.

26. The catheter introducer of claim 24, wherein the body is formed from a material comprising a polymeric material.

27. The catheter introducer of claim 24, wherein the slit segment is a first slit segment, and wherein the weakened portion of the tubular wall further comprises a second slit segment that is axially aligned with the first slit segment and the scored segments and that is located between the second scored segment and the proximal end of the tip.

28. The catheter introducer of claim 24, wherein the weakened portion of the tubular wall includes at least two slit segments and at least two scored segments which are disposed in an alternating aligned abutting relationship with one another.

29. The catheter introducer of claim 24, wherein the tubular wall has a second weakened portion and which is circumferentially offset from the first weakened portion.

30. The catheter introducer of claim 24, wherein the two weakened portions are offset from one another by about 180°.

31. The catheter introducer of claim 24, wherein the slit segments extend at least essentially through the depth of the tubular wall.

32. The catheter introducer of claim 24, wherein the slit segments extend through at least about 99% of the depth the tubular wall.

33. The catheter introducer of claim 24, wherein the scored segments extend through about 10% of the depth of the tubular wall.

34. The catheter introducer of claim 24, wherein the scored segment extends through about 20% of the depth of the tubular wall.

35. A method of inserting a medical device having a larger outer diameter than an inner diameter of a catheter tip of a catheter introducer through an opening in the catheter tip, the method comprising:
(a) cannulating a vein or artery with a needle and the catheter introducer, the catheter introducer being disposed over the needle and the catheter introducer including an expandable tip on a distal end thereof, the expandable tip including
(i) a body including an outer surface defining a lumen and having a distal end and a proximate end; and;
(ii) an expandable tip on the distal end, the expandable tip including an opening axially extending therethrough and an axially extending weakened portion formed from (1) at least one slit segment and (2) at least first and second scored segments that are axially aligned with each other and with the slit segment, the first scored segment being positioned between a proximal-most slit segment and a proximal end of the expandable tip, and the second scored segment extend from a distal-most slit segment to a distal end of the expandable tip;
(b) removing the needle from the catheter introducer;
(c) inserting a medical device into the body, the device having a larger outer diameter than a minimum inner diameter of the expandable tip;
(d) inserting the medical device through the lumen of the body; and
(e) inserting the medical device through the opening of the expandable tip, thereby expanding the expandable tip as a result of the insertion of the medical device through the tip; and then
(f) removing the catheter introducer from the patient's body while leaving the device in place.

36. The method of claim 35, wherein the device comprises a guidewire.

37. The method of claim 36, further comprising, after the removing step, inserting a peripheral or central venous or arterial device over the guidewire and into the vein or artery, and then removing the guidewire from the peripheral or central venous or arterial device.

38. The method of claim 37, wherein the peripheral or central venous or arterial device comprises a PICC line.

39. The method of claim 38, wherein the expanding step comprises splitting the distal end of the expandable tip at least one of the weakened portions and expanding a width of at least one of the slit segments.

* * * * *

UNITED STATES PATENT AND TRADEMARK OFFICE
CERTIFICATE OF CORRECTION

PATENT NO.       : 7,144,386 B2  Page 1 of 1
APPLICATION NO.  : 10/634715
DATED            : December 5, 2006
INVENTOR(S)      : Korkor et al.

It is certified that error appears in the above-identified patent and that said Letters Patent is hereby corrected as shown below:

CLAIM 14          Replace the word "proximate" with --proximal--.
Col. 14, Line 1

CLAIM 18          Replace the word "at" with --adjacent--.
Col. 14, Line 61

CLAIM 35          Replace the word "proximate" with --proximal--.
Col. 16, Line 26

Signed and Sealed this

Twentieth Day of February, 2007

JON W. DUDAS
*Director of the United States Patent and Trademark Office*